(12) United States Patent
Lugtigheid

(10) Patent No.: US 7,207,332 B1
(45) Date of Patent: Apr. 24, 2007

(54) APPARATUS FOR ADMINISTERING A GAS TO A PERSON OR AN ANIMAL

(76) Inventor: Gerardus Wilhelmus Lugtigheid, Dilledonk Noord 23, Spijkenisse (NL), NL-3206 BW ( * ) Notice: Subject to any disclaimer, the term of this patent is extended or adjusted under 35 U.S.C. 154(b) by 0 days.

(21) Appl. No.: 10/220,888

(22) PCT Filed: Mar. 7, 2000

(86) PCT No.: PCT/NL00/00149

§ 371 (c)(1),
(2), (4) Date: Sep. 6, 2002

(87) PCT Pub. No.: WO01/66175

PCT Pub. Date: Sep. 13, 2001

(51) Int. Cl.
*A61M 16/00* (2006.01)

(52) U.S. Cl. .................. 128/204.28; 128/204.26; 128/205.13; 128/204.18; 128/205.24

(58) Field of Classification Search ............ 128/203.11, 128/203.26, 204.28, 205.13, 205.14, 205.15, 128/205.16, 205.17, 205.24, 204.26, 204.18; 137/907, 908, 102
See application file for complete search history.

(56) References Cited

U.S. PATENT DOCUMENTS

| | | | | |
|---|---|---|---|---|
| 3,088,477 A | * | 5/1963 | Bloom | ................... 137/512.2 |
| 4,082,093 A | | 4/1978 | Fry et al. | |
| 4,088,131 A | * | 5/1978 | Elam et al. | ............ 128/205.13 |
| 4,121,580 A | * | 10/1978 | Fabish | .................... 128/205.11 |
| 4,207,884 A | * | 6/1980 | Isaacson | ................ 128/200.24 |
| 4,249,528 A | | 2/1981 | Mathes | ................... 128/205.13 |
| 4,374,521 A | | 2/1983 | Nelson et al. | ......... 128/205.13 |
| 4,823,828 A | | 4/1989 | McGinnis | |
| 4,856,548 A | | 8/1989 | Paluch | |
| 5,109,840 A | | 5/1992 | Daleiden | |
| 5,127,896 A | | 7/1992 | de Gaston | .................... 600/20 |
| 5,398,714 A | * | 3/1995 | Price | .......................... 137/102 |
| 5,558,371 A | * | 9/1996 | Lordo | ......................... 285/114 |
| 5,632,298 A | * | 5/1997 | Artinian | ..................... 137/102 |

* cited by examiner

*Primary Examiner*—Henry Bennett
*Assistant Examiner*—Annette Dixon
(74) *Attorney, Agent, or Firm*—Young & Thompson

(57) ABSTRACT

An apparatus (1) for administering a gas to a person or an animal, is provided with a chamber (9) for receiving a quantity of gas to be administered. The chamber is provided with a gas line (3) for supplying gas from a source to the chamber (9) and elements for pressurizing the gas in the chamber. The chamber (9) is connected to a breathing tube (5) for supplying pressurized gas from the chamber (9) to the person or the animal, wherein the breathing tube (5) connects to a discharge channel (26), for discharging gas exhaled by the person or the animal, via a valve (11), which restricts the flow of exhaled gas from the breathing tube (5) to the discharge channel (26) in order to build up gas pressure in the breathing tube (5) during exhalation.

19 Claims, 4 Drawing Sheets

APPARATUS FOR ADMINISTERING A GAS TO A PERSON OR AN ANIMAL

BACKGROUND OF THE INVENTION

1. Field of the Invention

The present invention relates to an apparatus for administering a gas to a person or an animal, provided with a chamber for receiving a quantity of gas to be administered, which chamber is provided with a gas line for supplying gas from a source to the chamber and means for pressurising the gas in the chamber, the chamber connecting to a breathing tube for supplying pressurised gas from the chamber to the person or the animal.

2. Description of the Related Art

Ventilators of the type specified in the preamble are known in the prior art. Such ventilators are used for ventilating patients. A certain quantity of gas is received in a chamber, after which the gas is brought under elevated pressure. As a result of raising the pressure, a flow channel is opened from the chamber to the breathing tube which is connected to the apparatus. The gas is administered to the patient via this breathing tube. The gas pressure in the chamber and, consequently, in the breathing tube is then lowered. The patient is given the opportunity to breathe out. The gas flow of the exhaled gas is now fed via the breathing tube to a discharge channel to discharge the gas from the apparatus.

For numerous applications it is desirable that the gas supplied to the patient remains in the patient's respiratory tract for a prolonged period. Moreover, it is desirable if this gas is kept under a certain minimum pressure in the patient's lungs. It is not possible with the aid of the apparatus according to the prior art to choose a threshold value which must be exceeded in the patient's lungs before the patient is able to exhale the inhaled air via the breathing apparatus.

SUMMARY OF THE INVENTION

The aim of the present invention is to provide an apparatus of the type specified in the preamble with which a patient is able to exhale inhaled air only when the pressure of this air in the lungs and the breathing tube is in excess of a certain minimum.

This aim is achieved in the present invention in that the breathing tube connects to a discharge channel, for discharging gas exhaled by the person or the animal, via a valve, which valve restricts the flow of the exhaled gas from the breathing tube to the discharge channel in order to build up gas pressure in the breathing tube during exhalation.

As a result of this measure it is possible to retain inhaled air longer in the lungs and to ensure that a certain pressure build-up takes place in the lungs before the inhaled air can be exhaled again.

The apparatus according to the invention is further improved in that the apparatus contains means for adjusting the degree to which the valve shuts off the flow of gas from the breathing tube to the discharge channel. As a result of this measure it is possible to set the threshold value depending on the desired objective.

The apparatus is further improved in that the valve is constructed as a movable wall which separates the chamber from an inlet opening for the breathing tube and for the discharge channel, wherein the movable wall of the chamber is movable between a first position, in which the wall is forced against the inlet end of the breathing tube and consequently shuts off the breathing tube, and a second position, in which the wall exposes the inlet end of the breathing tube, the outlet end of the breathing tube being brought into open communication with the discharge channel, wherein the position of the wall between the first and the second position thereof is determined by the instantaneous pressure differences in the chamber and in the breathing tube, wherein one or more channels and a shut-off element are provided in the movable wall, which shut-off element is movable between a closed position, in which the shut-off element shuts off the channels in the movable wall, and an open position, in which the shut-off element exposes the channels in the movable wall, wherein the position of the shut-off element is determined by instantaneous pressure differences in the chamber and the breathing tube, wherein the shut-off element is forced into the open position thereof when the instantaneous pressure in the chamber exceeds a threshold value. Furthermore, it is possible for the apparatus to be provided with pretensioning means for forcing the movable wall into the first position.

In the apparatus according to the prior art the movable wall, and the shut-off element provided therein, is used for guiding the gas stream through the apparatus in the correct manner. At an elevated gas pressure in the chamber the communication between the outlet end of the breathing tube and the discharge channel is shut off with the aid of the movable wall. Under the influence of the elevated pressure in the chamber, the shut-off element is forced into the open position thereof, so that the gas can pass from the chamber into the breathing tube. When the patient exhales, the movable wall is moved into the second position thereof, so that there is open communication between the breathing tube and the discharge channel. The shut-off element in the movable wall is forced into the closed position thereof, so that the gas exhaled by a patient cannot flow back into the chamber. The gas exhaled by the patient is guided via the breathing tube and the discharge channel in the direction of the discharge, with the aid of which the gas is discharged from the apparatus.

According to the invention, it is furthermore possible that the pretensioning means comprise a spring. It is furthermore possible that the pretensioning force of the pretensioning means is adjustable manually with the aid of a dial.

As a result of these measures, an adjustable pretensioning force on the movable wall is provided with the aid of very simple means. Consequently the apparatus according to the invention is relatively simple to produce. This makes it possible also to use the apparatus in countries where technical development is less advanced. Furthermore, the construction of the apparatus according to the invention is relatively simple and thus inexpensive.

The apparatus according to the invention is further improved in that the chamber is provided with a safety valve which exposes a passage between the chamber and a discharge from the apparatus as soon as the pressure in the chamber exceeds a threshold value. In this context it is possible for the safety valve to be provided with pretensioning means, the pretensioning of which is adjustable manually by means of an adjusting knob.

The presence of the safety valve prevents gas from the chamber being supplied at too high a pressure to the patient. As a result of the fact that the pretensioning force on the safety valve is adjustable, the maximum pressure in the chamber can be adjusted per patient. The fact that the adjustment force can be adjusted manually makes the apparatus simple to operate, even by less highly trained personnel.

Furthermore, it is possible according to the invention for the apparatus to be provided with a measurement channel, which connects to the breathing tube, a connection for a pressure gauge being provided in the measurement channel.

According to the invention it is possible that the means for pressurising the gas in the chamber comprise an element that is compressible by hand, such as a balloon. The user provides for pressure build-up by squeezing the balloon.

BRIEF DESCRIPTION OF THE DRAWINGS

The invention will be further described with reference to the appended figures, in which.

DESCRIPTION OF THE PREFERRED EMBODIMENTS

Figure 1:
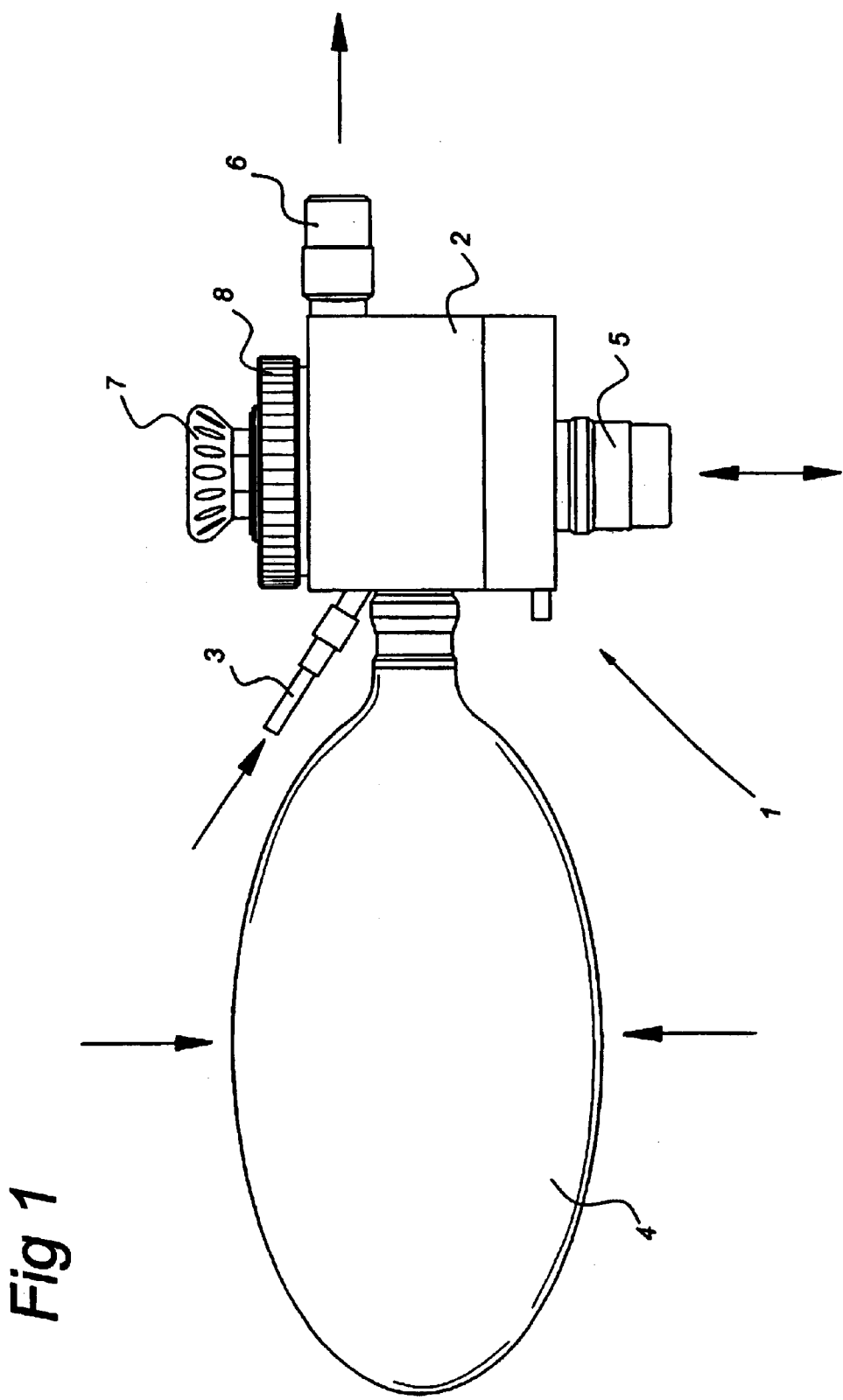
FIG. 1 is a view of the apparatus according to the invention.

The apparatus 1 according to the invention is shown in FIG. 1. The apparatus 1 comprises a housing 2 in which a chamber for receiving gas is delimited (see FIG. 2). The housing 2 is provided with a gas line 3, which can be connected to a source (not shown) for supplying gas to the housing 2. The apparatus 1 further comprises a balloon 4. This balloon 4 can be compressed by hand (in the direction of the arrows shown in the figure) to pressurise gas that has been received in the housing 2. Gas can be discharged from the housing 2 via the breathing tube 5. In use, this breathing tube 5 is fed to a patient who has to be ventilated with the aid of the apparatus 1. When a patient exhales gas this gas is fed back to the housing 2 via the breathing tube 5. As a result of the presence of discharge channels (explained with reference to FIG. 2 et seq.), exhaled gas is fed via a discharge channel 26 to a discharge 6, which discharges said exhaled gas from the apparatus 1.

Furthermore, the apparatus is provided with an adjusting knob 7, with the aid of which a pretensioning force can be set on a safety valve 30. The apparatus further comprises a dial 8, with the aid of which the pressure which a patient must overcome to be able to exhale gas via the apparatus is set. The functioning of the adjusting knob 7 and the dial 8 is explained in detail with reference to FIG. 2.

Figure 2:
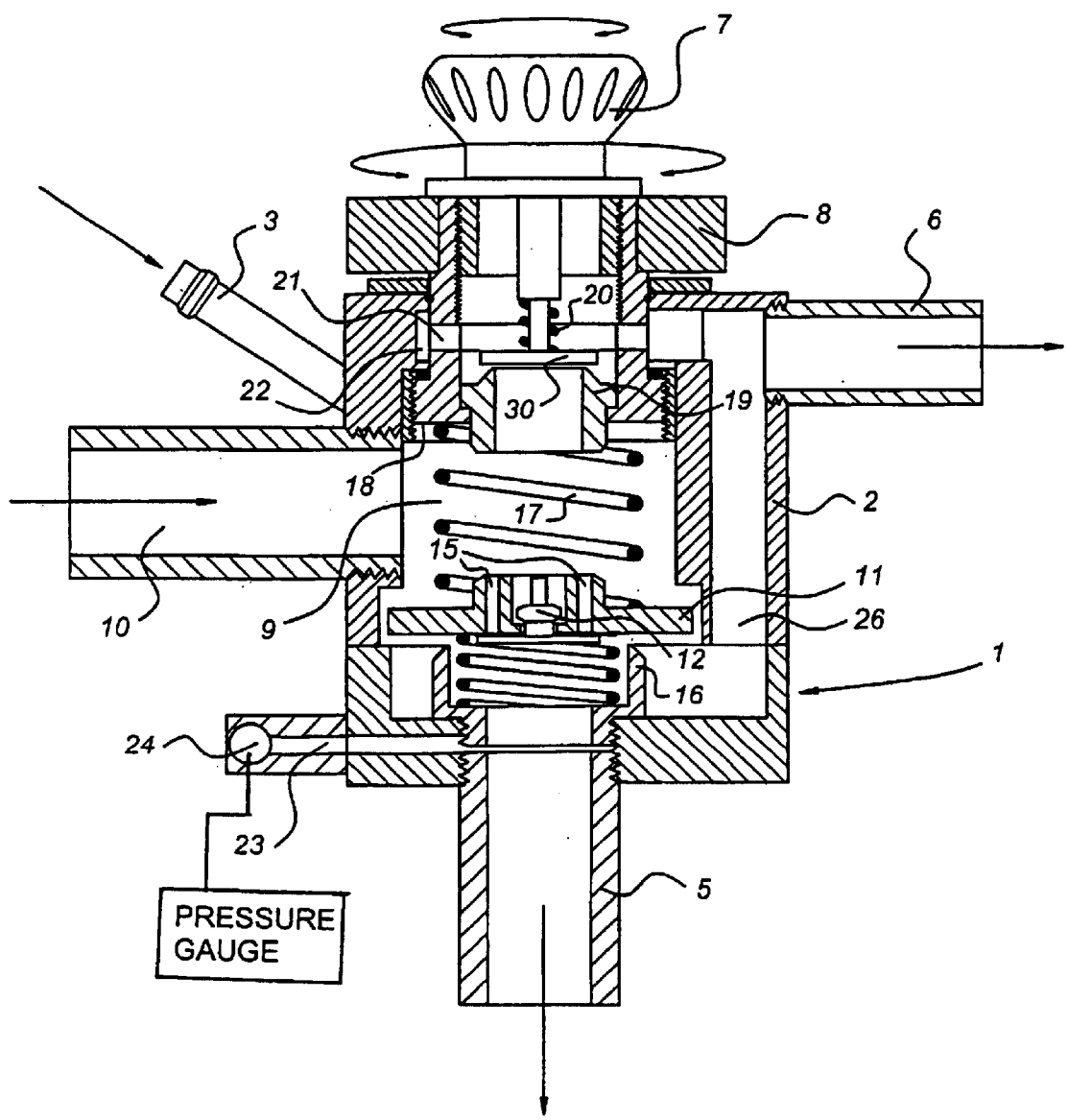
FIG. 2 is a cross-section of the apparatus according to FIG. 1.
Figure 3:
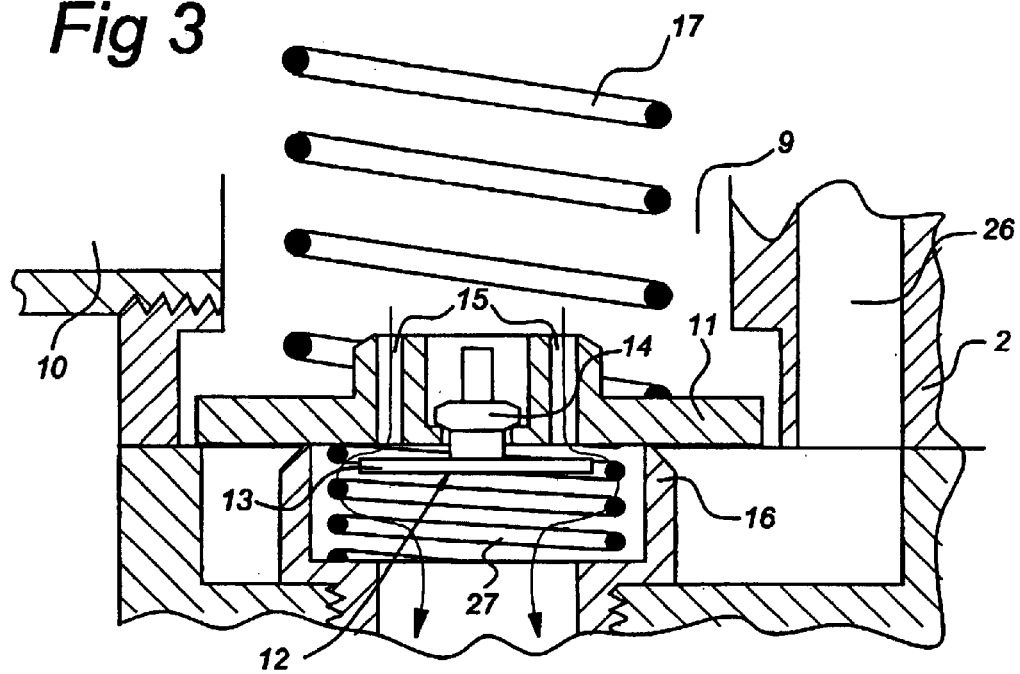
FIG. 3 shows a detail of the cross-section in FIG. 2, in the position where gas is fed from the chamber to the breathing tube.
Figure 4:
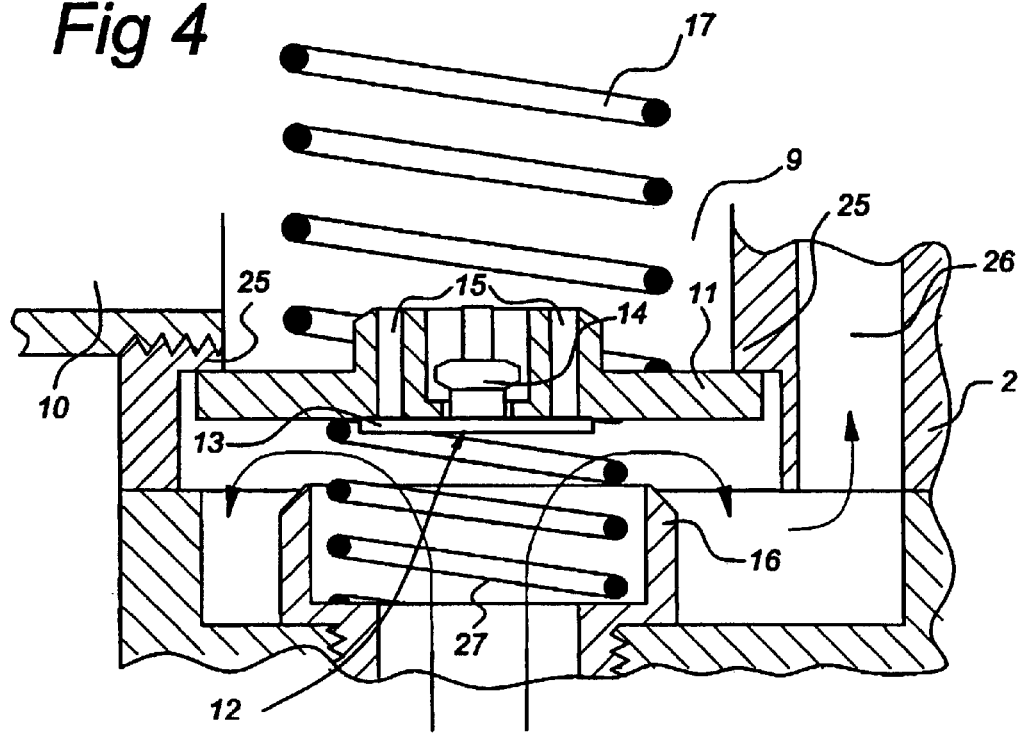
FIG. 4 shows a detail of the cross-section in FIG. 2, in the position where gas is fed from the breathing tube to a discharge channel.

FIG. 2 shows a cross-section of the apparatus according to FIG. 1. A chamber 9, in which a quantity of gas to be administered can be received, is delimited in the housing 2. The chamber 9 is in open communication with the balloon 4 (not shown) via a line 10. Via the line 10 gas can be forced from the balloon 4 under elevated pressure into the chamber 9. The chamber 9 is provided at the bottom thereof with a movably mounted wall 11. The wall 11 is movable between two extreme positions which are shown in FIGS. 3 and 4, respectively. The inlet 16 of the breathing tube 5 is located underneath the movable wall 11. The inlet 16 is separated from the chamber 9 by the wall 11. A discharge channel 26, for discharging exhaled air in the direction of the discharge 6, is also located underneath the movable wall 11. One or more channels 15 have been made in the movable wall 11 itself, which channels can be shut off by means of a shut-off element 12.

When building up gas pressure in the chamber 9 the movable wall 11 is forced, with the aid of the spring 17, against the inlet 16 of the breathing tube 5. In this position the communication between the breathing tube 5 and the discharge channel 26 is shut off. When the pressure in the chamber is then raised the shut-off element 12 will move down. As a result the channels 15 in the movable wall 11 are exposed, so that gas transport can take place from the chamber 9 in the direction of the breathing tube 5. This position is shown in FIG. 3. It can be seen in FIG. 3 that the wall 11 is in contact with the inlet 16 of the breathing tube 5. The shut-off element 12 has moved down and the shut-off element 12 is held in the position shown because a ridge 14 is in contact with a projecting section of the wall 11. In the position shown the shut-off face 13 of the shut-off element 12 is free from the channels 15 in the wall 11. Consequently fluid transport can take place through the wall 11 in the direction of the breathing tube 5. Opening of the channels 15 can be promoted by making the shut-off face 13 of the shut-off element 12 of a relatively flexible material, such as rubber. In this case the outermost edges of the shut-off face 13 are able to bend, so that the channels are exposed to a considerable extent. Since the movable wall 11 is in contact with the inlet 16 of the breathing tube 5, the open connection between the breathing tube 5 and the discharge channel 26 is shut off. As a result air from chamber 9 is prevented from passing into the discharge channel 26. The shut-off element 12 is connected to a spring 27. With the aid of this spring the movable wall 11 can be placed under a certain pretension. The shut-off element 12 exposes the channels 15 in the movable wall 11 only at a point in time when a specific threshold value is exceeded.

FIG. 4 shows the case where the movable wall 11 has moved into the second position thereof. The movable wall 11 can assume this position when the pressure in the breathing tube becomes higher than that in the chamber 9. This position is assumed when the patient exhales. A patient cannot get the wall 11 into the position shown in FIG. 4 simply by exhaling. In order to be able to move the wall into this position a certain threshold value must be exceeded, which is determined by the pretensioning force that is exerted on the wall 11 by means of the difference between springs 17–27. The higher the pretensioning force of the spring 17 on the wall 11, the higher must be the pressure in the breathing tube in order to be able to move the wall into the position shown. It can be seen from FIG. 4 that in the position shown there is a free passage between the outlet end 16 of the breathing tube 5 and the discharge channel 26. This means that the patient can blow out the exhaled air via the breathing tube 5 and the discharge channel 26 connected thereto in the direction of the discharge 6 of the apparatus (see FIG. 2). It can also be seen in FIG. 2 that the shut-off element 12 shuts off the channels 15 in the movable wall 11. This means that the exhaled air cannot pass into the chamber 9. The shut-off face 13 of the shut-off element 12 is in contact with the openings of the channels 15 and so prevents fluid transport from the breathing tube 5 in the direction of the chamber 9. The extreme position of the movable wall 11 is delimited by ridges 25 which project from the wall of the chamber 9.

The function of the spring 17 is described with reference to FIGS. 3 and 4. It can be seen in FIG. 2 that the pretensioning force on the spring 17 is adjustable with the aid of a dial 8. This dial can be turned by hand, so that a stop face 18, against which the end of the spring 17 bears, can be moved relative to the wall 11. Depending on the desired objective and depending on the expiration force (pressure that can be built up by a patient) of a patient, a certain pretension can be applied to the spring 17. Because the pretensioning force on the spring 17 is adjustable by hand, the apparatus 1 according to the invention is easy to use. A correct setting can, for example, be guaranteed by providing a scale on the apparatus and/or on the dial 8.

It can also be seen in FIG. 2 that the top wall of the chamber 9 comprises a hollow body 19. This hollow body 19 is closed off at the top by means of a valve 30. This valve 30 serves as a safety valve. If the pressure in the chamber 9 becomes too high the safety valve 30 is forced upwards so that free communication is produced between the chamber 9 and openings 21–22 which have been made in the rotary body that is connected to the dial 8. The air can escape from the chamber 9 via these openings 22 and be fed to the discharge 6. This prevents gas under too high a pressure being supplied to a patient via the breathing tube 5. The maximum pressure that can be reached in the chamber 9 can be set by adjusting the pretension on the valve 30. This pretension is achieved with the aid of a spring 20. The pretension of the spring 20 can be adjusted by means of a rotary knob 7. This knob 7 can also be operated by hand.

Figure 5:
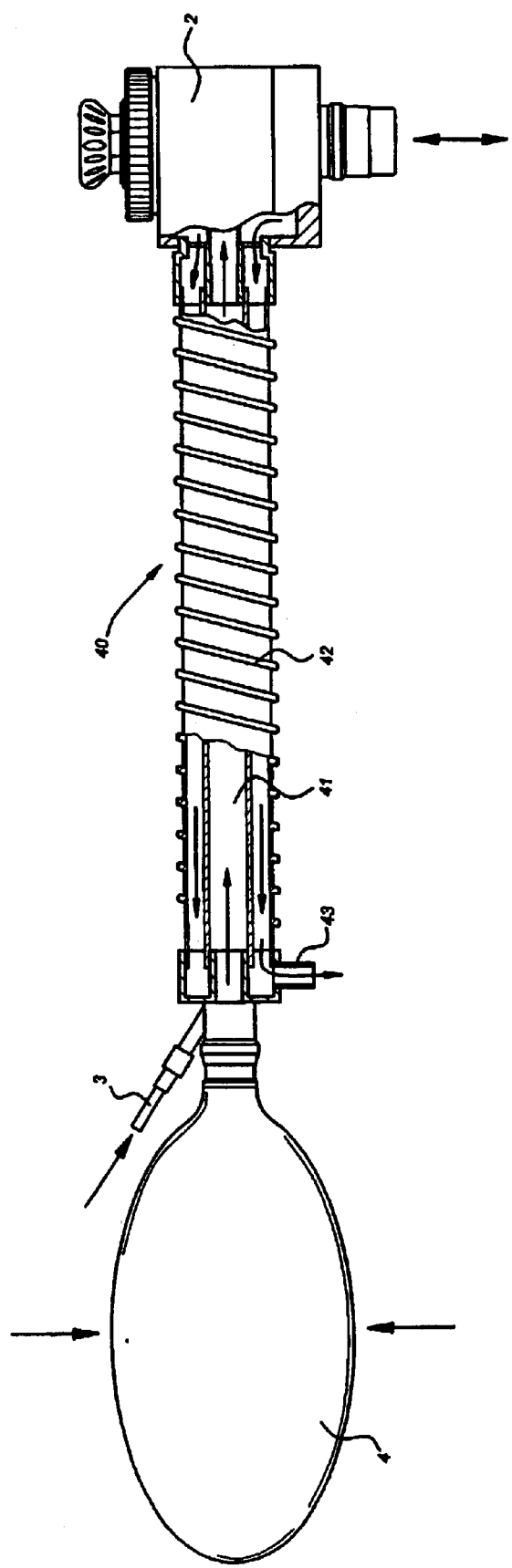
FIG. 5 illustrates a further embodiment of the ventilator.

A further embodiment of the ventilator according to the invention is shown in FIG. 5. According to FIG. 5 a hose 40 is arranged between the housing 2 and the balloon 4. As a result of the presence of the hose 40, a user is able to exert manual force on the balloon 4 whilst the balloon 4 is some distance away from the housing 2. This increases the ease of use of the apparatus according to the invention. Medical staff can, for example, operate the balloon 4 from the side of the patient's bed. According to FIG. 5 the gas line 3 is located at the end of the hose 40, that is to say some distance away from the housing 2. This too offers the option of coupling the gas supply to the apparatus according to the invention some distance away from the patient's mouth. The gas supply will usually have to be coupled to the gas line 3 from anaesthesia equipment or an anaesthesia wall set.

FIG. 5 furthermore shows the case where the hose 40 has an inner line 41 which connects the balloon 4 to the housing 2. The line 41 is used to supply fresh gas in the direction of the housing. The line 41 is enclosed by a second line 42. This line 42 is used as discharge line. The line 42 terminates in a discharge opening 43. As a result of the coaxial construction of the supply line for the gas and the discharge line for the gas, only one hose has to be fed from equipment in the direction of the patient. This application further increases the ease of use of the apparatus according to the invention.

Instead of the balloon shown in FIGS. 1 and 5, use can also be made of the so-called "rigid balloon". A rigid balloon is a balloon which is provided with a valve. After the force for squeezing the balloon is removed, the balloon will assume its original shape again. During this movement the valve in the rigid balloon will be opened to draw in a quantity of fresh gas (ambient air).

For the sake of clarity it is pointed out that the apparatus shown in the figures can be produced in various sizes. For instance, a system can be made with smaller dimensions which is especially suitable for children or neonates. In this case the lines will also be made smaller.

With the aid of the adjustable force on the safety valve 30 it is possible to set a maximum pressure in the chamber 9 of, for example, 20–60 cm $H_2O$. The maximum pressure which a patient must overcome in order to be able to blow air out of the apparatus 1 can be set, for example, from 0 to 20 cm $H_2O$. In order to make the apparatus according to the invention also suitable for children, the aim is to keep the dead volume in the apparatus as small as possible. By means of the construction as is shown in FIGS. 1 to 4 it is possible to achieve a dead volume of typically at most 7 ml.

The connection of the balloon to the apparatus 1 via the line 10 can, for example, be made using a so-called balloon cone with an external diameter of 22 mm.

The discharge 6 can be constructed as an evacuation cone of 19 mm.

The breathing tube 5 can be constructed as a cone of 22/15 mm.

The apparatus according to the invention is provided with a self-closing 24 measurement channel 23 which connects to the breathing tube 5. A pressure gauge can be fitted in this measurement channel in order to be able to measure the instantaneous pressure in the breathing tube 5. The pressure gauge can be constructed as a manometer or as an electronic measuring device. Furthermore, it is possible to fill the chamber 9 with the aid of a pump, for example a time-controlled pump, instead of a balloon. In this way a constant flow from the chamber to the breathing tube can be guaranteed while a patient is inhaling.

The movable wall 11 can be made of various types of materials. As an alternative, the moveable wall can also be constructed as a flexible plate clamped in place. In this case the moveable wall forms a membrane that is movable to and fro.

What is claimed is:

1. Apparatus for administering a gas to a person or an animal, comprising:
   a chamber having an inlet;
   means for supplying the gas under pressure to the chamber inlet;
   a breathing tube connected to the chamber through a breathing valve, the breathing valve constructed to allow the gas to pass from the chamber to the breathing tube, and to allow exhaled gas in the breathing tube to pass from the breathing tube to outside the apparatus;
   an aperture through which the gas in the chamber can pass to outside the apparatus; and
   a safety valve separrate from the breathing valve, the safety valve being urged by a first spring pressure to close the aperture;
   wherein the safety valve is constructed and arranged to allow the gas in the chamber to escape through the aperture to outside the apparatus as soon as pressure of the gas in the chamber exceeds a threshold value, the threshold value being determined by the first spring pressure; and
   wherein the first spring pressure is adjustable over a predetermined range.

2. The apparatus of claim 1, wherein the breathing valve is urged by a second spring pressure separate from the first pressure into a position that prevents the exhaled gas in the breathing tube from passing from the breathing tube to outside the apparatus, the exhaled gas being allowed to pass from the breathing tube to outside the apparatus so long as froce exerted by the exhaled gas exceeds a force exerted by the second spring pressure.
   wherein the second spring pressure is adjustable over a predetermined range.

3. The apparatus of claim 2, wherein the first and second spring pressures are adjustable independently of one another.

4. The apparatus of claim 3, wherein the first and second spring pressures are adjustable by respective rotatable dials.

5. The apparatus of claim 1, wherein the first spring pressure is adjustable over a range of 20-60 cm H$_2$O.

6. The apparatus of claim 1, wherein the breathing valve is constructed and arranged such that the gas that passes from the breathing tube through the breathing valve cannot flow back into the chamber.

7. The apparatus of claim 1, wherein the safety valve comprises a threaded element attached to the apparatus so that rotation of the threaded element cuasuses a change to the first spring pressure within the predetermined range.

8. The apparatus of claim 7, wherein the threaded element is a rotary knob, and the spring pressure is provided by a spring that is operably connected to the rotary knob so that rotation of the rotary knob cuases a change to a pretension of the spring.

9. The apparatus of claim 1, wherein the means for supplying the gas under pressure is a means for manually pressurizing the gas.

10. The apparatus of claim 1, wherein the safety valve is constructed and arranged so as to connect directly to the chamber.

11. The apparatus of claim 1, further comprising a discharge opeining disposed on the apparatus so that both the exhaled gas that passes through the breathing valve and the gas in the chamber that passes through the safety valve pass outside the apparatus by way of the discharge opeining.

12. The apparatus of claim 1, further comprising a measurement channel connected to the breathing tube, the measurement channel comprising a connection for a pressure gauge.

13. Apparatus for administering a gas to a person or an animal, comprising:

a chamber having an inlet;

means for supplying the gas under pressure to the chamber inlet;

a breathing tube connected to the chamber through a breathing valve, the breathing valve constructed to allow the gas to pass from the chamer to the breathing tube, and to allow exhaled gas in the breathing tube to pass from the breathing tube to outside the apparatus;

an aperture through which the gas in the chamber can pass to outside the apparatus; and a safety valve separate from the breathing valve, the safety valve being urged by a first spring pressuer to close the aperture, the safety valve being constructed and arranged to allow the gas in the chamber to escape through the aperture to outside the apparatus as soon as pressure of the gas in the chamber exceeds a threshold value, the threshold value being determined by the first spring pressure; and a discharge opeing disposed on the apparatus so that both the exhaled gas that passes through the breathing valve and the gas in the chamber that passes through the safety valve pass outside the apparatus by way of the discharge opening.

14. The apparatus of claim 13, wherein the means for supplying the gas under pressure is a means for manually pressurizing the gas.

15. The apparatus of claim 13, wherein the safety valve is constructed and arranged so as to connect directly to the chamber.

16. The apparatus of claim 13, further comprising a measurement channel connected to the breathing tube, the measurement channel comprising a connection for a pressure gauge.

17. Apparatus for administering a gas to a person or an animal, comprising:

a chamber having an inlet;

means for supplying the gas under pressure to the chamber inlet;

a breathing tube connected to the chamber through a breathing valve, the breathing valve constructed to allow the gas to pass from the chamber to the breathing tube, and to allow exhaled gas in the breathing tube to pass from the breathing tube to outside the apparatus;

an aperture through which the gas in the chamber can pass to outside the apparatus; and a safety valve separate from the brathing valve, the safety valve being urged by a first spring pressure to close the aperture, the safety valve being constructed and arranged to allow the gas in the chamber to escape through the aperture to outside the apparatus as soon as pressure of the gas in the chamber exceeds a threshold value, the threshold value being determined by the first spring pressure; and a measurement channel connected to the breathing tube, the measurement channel comprising a connection for a pressure gauge.

18. The apparatus of claim 17, wherein the means for supplying the gas under pressuer is a means for manually pressurizing the gas.

19. The apparatus of claim 17, wherein the safety valve is constructed and arranged so as to connect directly to the chamber.

* * * * *